US00PP08753P

United States Patent [19]

Conrad

[11] Patent Number: Plant 8,753

[45] Date of Patent: May 31, 1994

[54] JENNIFER CONRAD ROSE BUSH

[76] Inventor: Jean Conrad, 1780 Marston Pl., Tallahassee, Fla. 32312

[21] Appl. No.: 929,901

[22] Filed: Aug. 17, 1992

[51] Int. Cl.[5] ..... A01H 5/00
[52] U.S. Cl. ..... Plt./5
[58] Field of Search ..... Plt. 5, 2

[56] Reference Cited

U.S. PATENT DOCUMENTS

PP 1951 6/1960 Moore ..... PLT/5
PP 6892 7/1989 Meilland ..... PLT/2
PP 8019 11/1992 Moore ..... PLT/2

*Primary Examiner*—James R. Feyrer
*Assistant Examiner*—E. F. McElwain
*Attorney, Agent, or Firm*—Franklin J. Cona

[57] ABSTRACT

The present invention relates to a new and unusually beautiful pillar type climbing rose bush. The primary feature of this new variety of pillar type climber rose bush is its vigorous growth and bushyness and the unusual coloration as it relates to the buds and the reddish tinge in the young stems.

6 Drawing Sheets

SUMMARY OF THE INVENTION

The present invention relates to a new and distinct variety of hardy climbing rose plant of the Floribunda class which bears semi-double flowers having golden stamens and pink petals with a creamy yellow zone near the center of the flower.

The variety is further characterized by the following: Flowers are borne on clusters of three to seven but sometimes more. The flowers also show a decrease in the pink color as it ages.

Blooms are pink, approximately 2.5 inches to 3 inches in diameter on average. They open flat. Blooms are deep pink when they first open but gradually decrease in color as they age. Just before the petals fall, the flower is almost white. As the blooming season progresses, the rose bush has an assortment of colors ranging from deep pink to light pink to almost white. The blooming started in mid April and had several flushes of blooms of roses through the end of June. After that, the flowers bloomed occasionally. After October, the plant became dormant. The above cited activity all occurred in Tallahassee, Fla.

The invention shows good resistance to black spots and powdery mildew. The invention responds well to commonly used fungicides. For example, Daconil and Funginex. The invention has been in Tallahassee for five years and has been through five frost cycles. To date there has been no adverse damage to the plant due to frost. The only apparent visibility degradation is a loss of some leaves. As far as susceptibility to insects, there is no known visible evidence of insect susceptibility as of this writing.

The present variety of climbing Floribunda was discovered by me in my garden at Tallahassee, Fla., as a sport from Climbing Summer Snow.

Subsequent to origination of the variety, asexual reproduction of the new variety by air layered cuttings derived from the plant stem as performed at Tallahassee, Fla., shows that the foregoing characteristics and distinctions come true to form and are established and transmitted through succeeding propagations.

The present variety differs from its parent:

Climbing Summer Snow—Upright, bush, white flowers.

Growth habit of Jennifer Conrad Rose Bush is similar to its parent.

The air-layering procedure to isolate the pink climber from the parent was done as follows:

Step 1. The air-layering was performed on a young branch originating approximately four feet from the base of a mature cane. A one inch cylinder of the outer layer of the bark of a young branch was removed.

Step 2. A rooting hormone with a fungicide (Roo-Tone) was smeared over the area were the bard of the stem was removed.

Step 3. Moist sphagnum moss was placed around the stem, and shaped in the form of an oval about three times the size of an egg. The sphagnum was held in place with a clear plastic wrap tied at both ends.

Step 4. Aluminum foil was placed over it to protect it from overheating by the sun.

Step 5. When roots penetrated the sphagnum, the branch was cut off at the base of the root growth and planted in the ground to form a new plant.

BRIEF DESCRIPTION OF THE PHOTOGRAPHS

The accompanying photographs show, as nearly true as it is reasonably possible to make the same in a color illustration of this character, typical specimens of plant parts of the new variety. The rose plants of the new variety described herein were grown in the open air at Tallahassee, Fla., USA.

FIG. 13 illustrates a specimen of a main branch;

FIG. 14 illustrates a specimen of a leaf with three leaflets—(a) under surface (b) upper surface;

FIG. 15 illustrates a specimen of a leaf with five leaflets—(a) upper surface (b) under surface;

FIG. 16 illustrates a specimen of a leaf with seven leaflets—(a) under surface (b) upper surface;

DETAILED DESCRIPTION

Figures 1, 2, 3, 4:
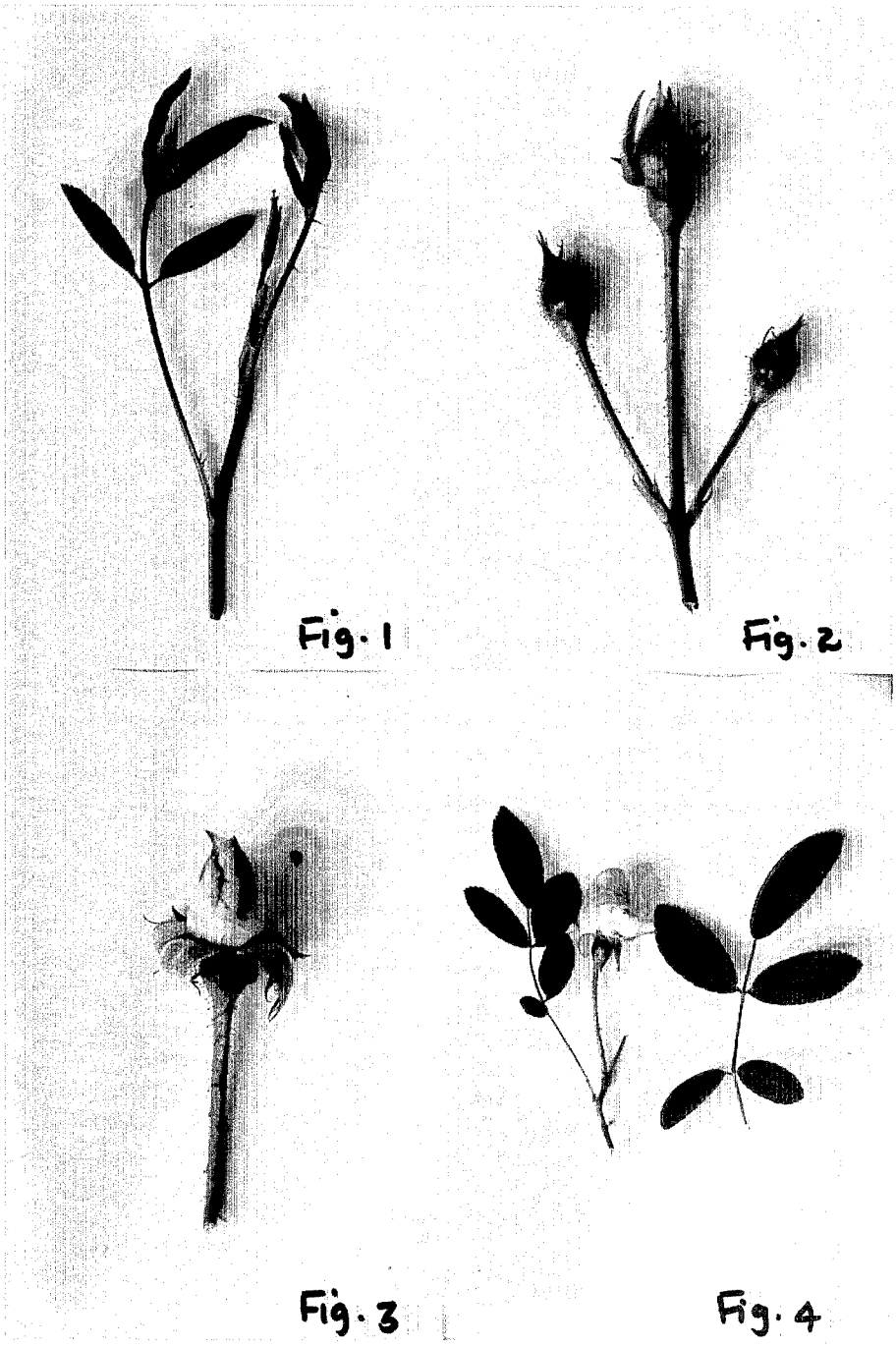
FIG. 1 illustrates a specimen of a young shoot.
FIG. 2 illustrates specimens of three floral buds before the opening of the sepals.
FIG. 3 illustrates a specimen of a floral bud at the opening of the sepals.
FIG. 4 illustrates a specimen of a floral bud as the petals open.
Figure 5:
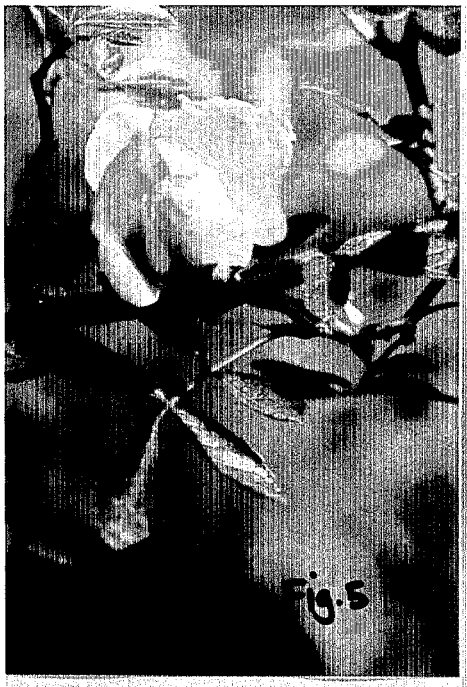
FIG. 5 illustrates a specimen of a flower in the course of opening.
Figure 6:
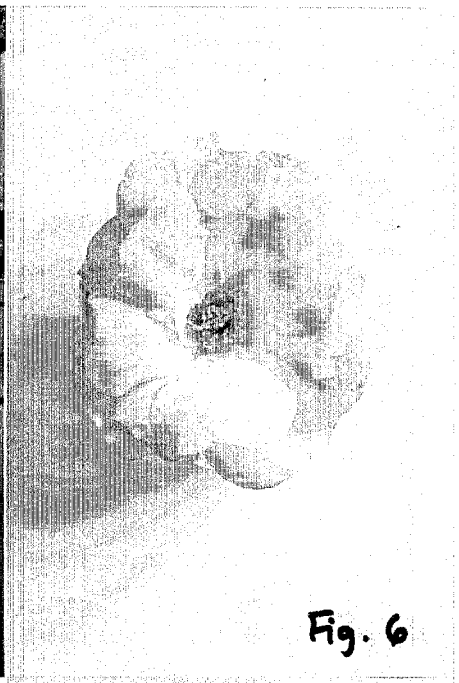
FIG. 6 illustrates a specimen of an open flower—plan view—obverse.
Figure 7:
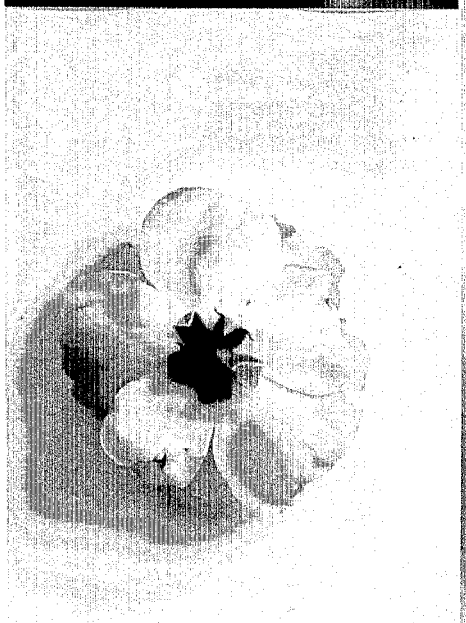
FIG. 7 illustrates a specimen of an open flower — plan view — reverse.
Figure 8:
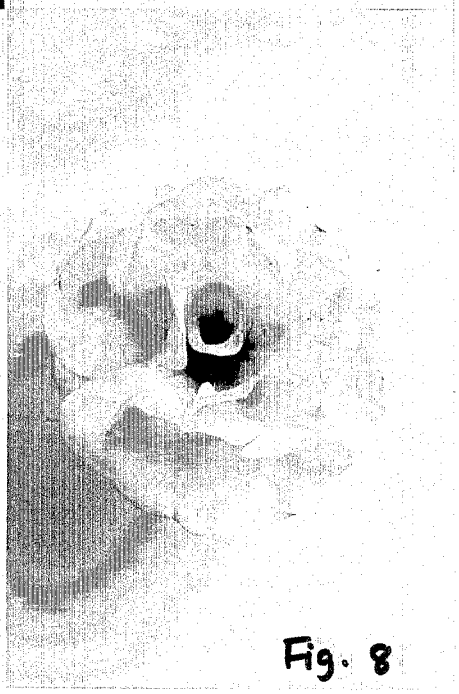
FIG. 8 illustrates a specimen of a fully open flower immediately prior to petal drop—plan view—obverse.
Figures 9, 10, 11, 12:
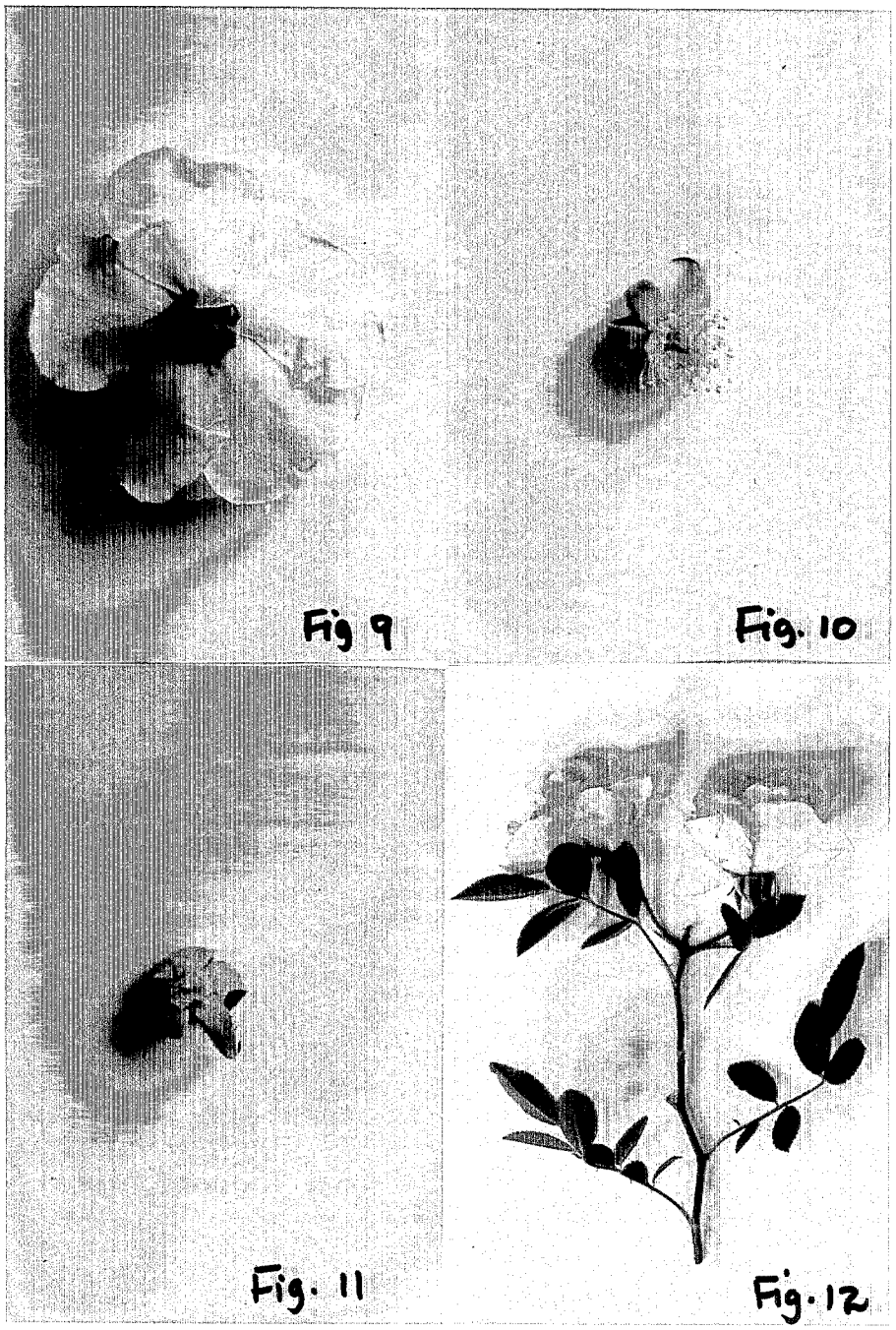
FIG. 9 illustrates a specimen of a fully open flower immediately prior to petal drop—plan view—reverse.
FIG. 10 illustrates a specimen of a floral receptable showing the arrangement of the stamens and the pistils.
FIG. 11 illustrates a specimen of a floral receptacle showing the arrangement of the pistils (stamens removed)
FIG. 12 illustrates a specimen of a flowering stem.
Figure 17:
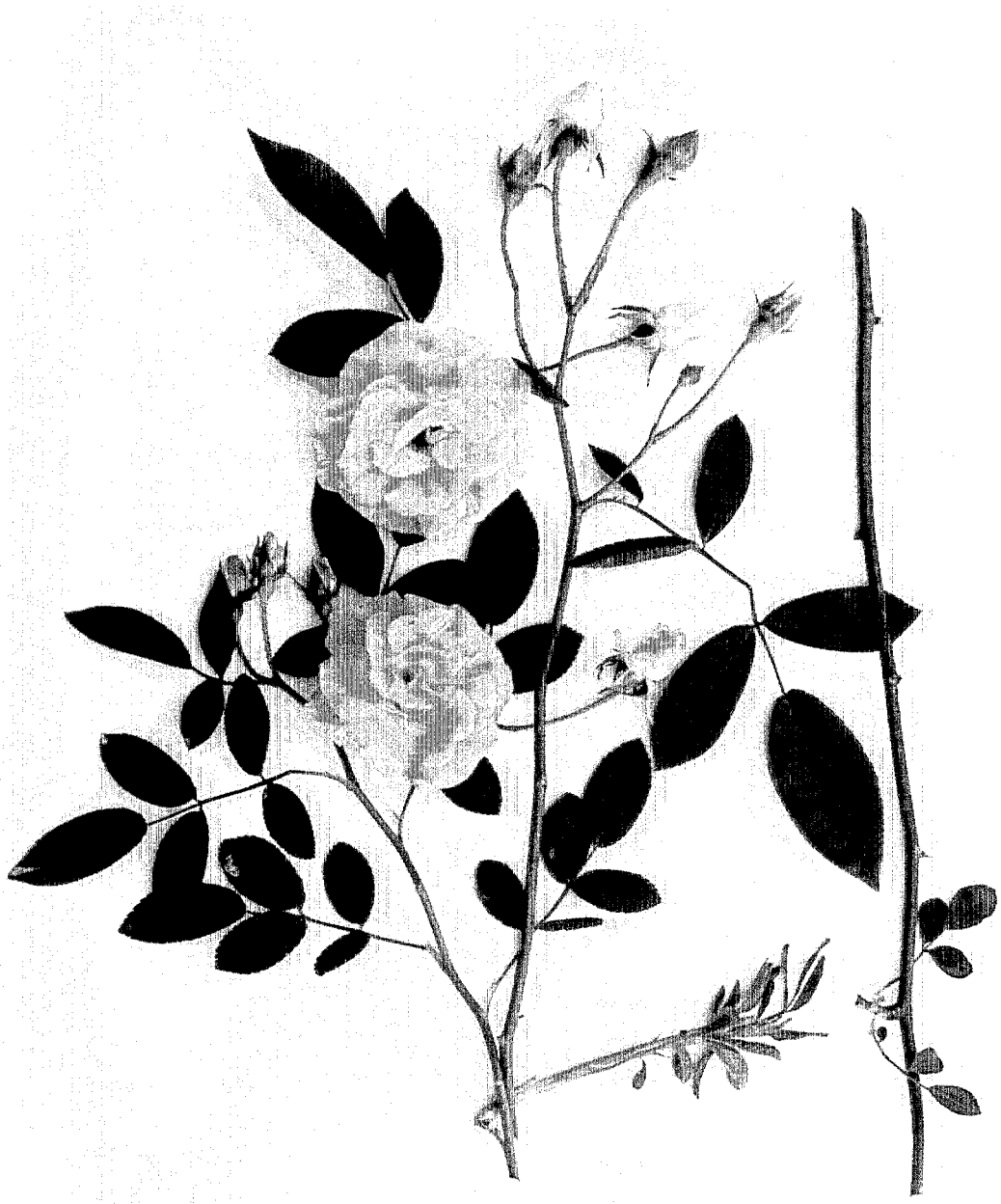
FIG. 17 illustrates specimens of flowers, leaves, buds and stems of the new rose variety.
Figure 18:
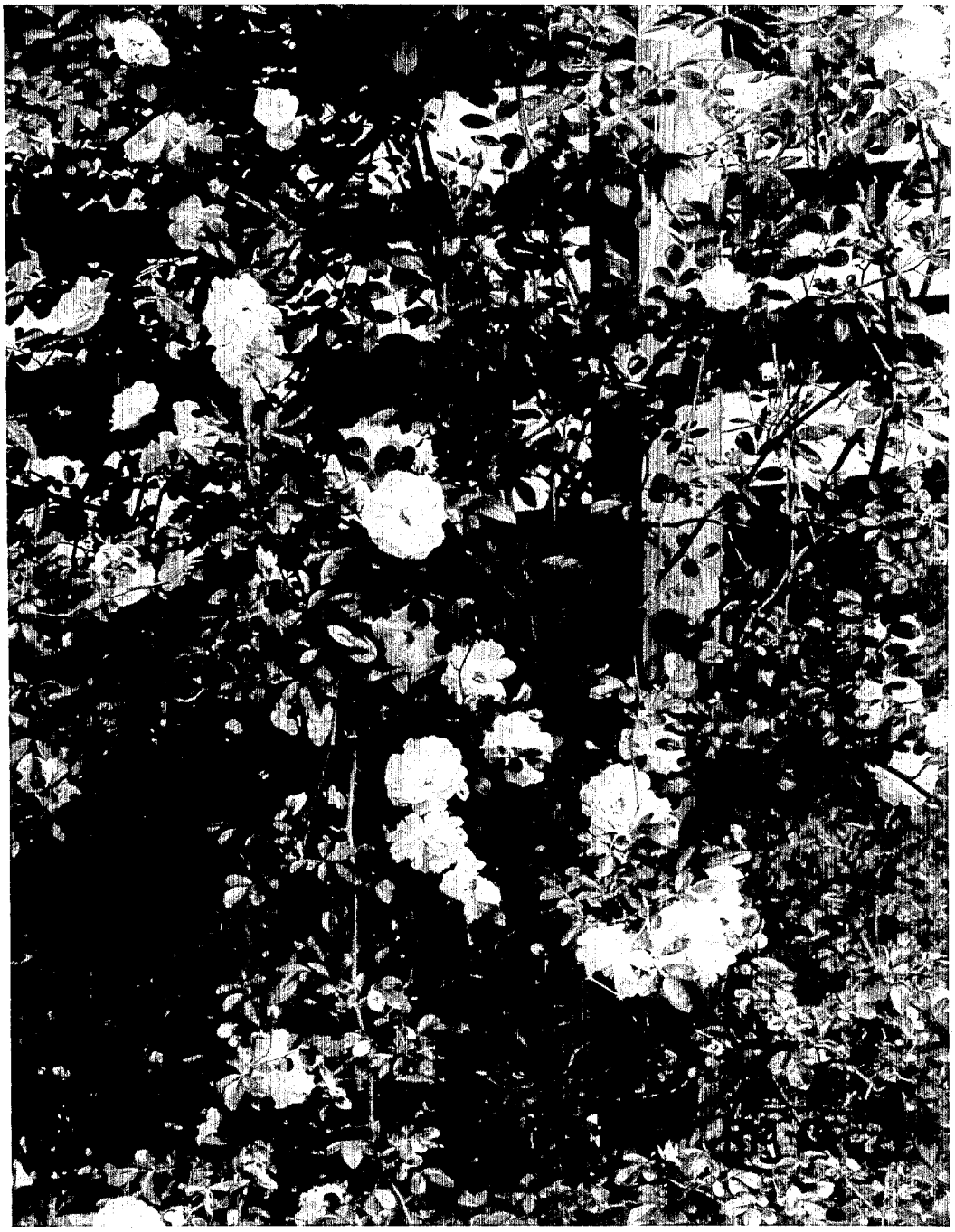
FIG. 18 illustrates an overall specimen of the new rose variety.

The chart used in the identification of colors is: Maerz, A. and M. Rea Paul, M. R., A Dictionary of Color, 1st. Edition. The description is based on two year old specimens of the new variety during April while grown in the open air at Tallahassee, Fla., USA.

Genus: Rosa.

Species: *Rosa multiflora.*

Class: Climbing shrub.

Plant:

*Height.*—Approximately 6 to 7 feet on average. Growth habit: The plant is vigorous and upright climber that can easily be trained on a pillar, trellis or fence and can grow to six or seven feet in height. The plant is very bushy and sprawling with dense green foliage. New canes start near the base of the plant, but new branches can arise from main canes. Mature stems are green but stems and leaves of very new growth at the ends of branches have a reddish tinge. Stems are essentially thornless — very seldom found on a stem, but leaf stems have small thorns. The thorns are on the underside of the leaf. The unusual thorns appear on the main stem on the underside of the stems having the leaves, either 3, 5 or 7 leaves. This is shown in great detail on FIG. 14 A and on FIG. 16 B where the thorns are very visible.

Branches:

*Color.*—Very young stems (at the end of branches) — light green with reddish tinge — Plate 7, Page 37, J8 (Domingo). Young stems — light green, Plate 21, Page 65, L5 (Grass Green). Mature stems — green — Plate 22, Pages 67, L5 (Cerro Green).

Leaves:

*Leaflets.*—Number: 3, 5, 7 (most often), Shape: oval, Serration: simple and regular, Texture: firm. Overall appearance: dense foliage with a glossy dark green aspect. Color of young foliage — Plate 22 Page 76, L5 (Cerro Green). Color of mature foliage — dark green — Plate 23, Page 69, A12 (Wintergreen, English Ivy+).

Flowers:

*Number of flowers.*—Clusters, generally 3 to 7 per stem but can have more.

*Blooming cycle.*—Starts late March and continues through June with profuse blooming. After June, the cycle repeats 6 to 8 weeks through October with only a few clusters of blooms.

*Fragrance.*—Very light.

*Form.*—Semi-double, opens flat, cupped form. Diameter: approximately 2.5 to 3 inches in diameter.

*Color.*—When opening begins, the upper surface shows a deep pink color, Plate 49, Page 121, G5 (Valencia), with a small creamy yellow zone, Plate 9, Page 41, E1, and F1, approximately one inch in diameter through the center of the flower. As the petals age, the pink color gradually fades to almost white. The deepest pink on the flower petals is G5, (Valencia). As the flowers age and fade, the color (Valencia), decreases gradually from G5 to G1 through B5 to B1 and A5 to A2.

*Petals.*—Petal count: 14 - 18 on average per flower. Petal count can be as high as 22 in blooming cycles that are not profuse. Petals on a cut flower last on an average 5 - 7 days before starting to fall. Petals on the uncut flower last 7 - 12 days on average before beginning to fall. The reverse side of the petals are lighter in color than in the front. Color intensity on the reverse decreases from the tip to the base with an almost white zone around the base in mature flowers.

*Petaloids.*—Very few per flower — usually only one.

*Buds.*—Ovoid in shape and very pale pink in color.

*Peduncle.*—Green Plate 20, Page 63, J8 — same color as bud, moderately prickly.

Reproductive organs:

*Stamens.*—Moderate number, regularly arranged around the pistils. They are more prominent than the pistils.

*Filaments.*—Short, strawlike, very pale yellow — sometimes with a greenish tinge.

*Pollen.*—Moderate amount, yellow in newly opened rose, turns dark brown as flower ages.

*Pistils.*—Moderate number.

*Styles.*—Short, even length, bunched together; color — very pale yellow, sometimes with a slight greenish tinge.

*Stigma.*—Height — extends to approximately the same level as the anthers on the stamens but slightly above the receptacle. Color — very pale yellow.

*Ovary.*—All enclosed in the calyx.

*Sepals.*—Five spear shaped sepals, usually even in size for an individual bud; size of sepal on bud — approx. ½ inch; size on a fully opened flower may vary up to 1". Sepals cover the bud completely but do not extend significantly beyond the bud. Upper surface — light green with whitish shading as it approaches the base. Lower surface — darker green, consistent with the color of the peduncle.

Development:

*Vegetation.*—Vigorous.

*Blossoming.*—Continuous, abundant in the spring.
*Aptitude to bear fruits.*—Few.
*Resistance to frost.*—Very good.
*Resistance to diseases.*—Good.

I claim:

1. A new and distinct variety of climbing shrub rose plant characterized by the following combination of characteristics:

(a) abundantly and continuously forms attractive long lasting double deep pink flowers with creamy yellow center and opens flat,
(b) exhibits vigorous vegetation,
(c) exhibits excellent resistance to frost, and
(d) is particularly well suited for growing in the landscape, substantially as herein shown and described.

* * * * *

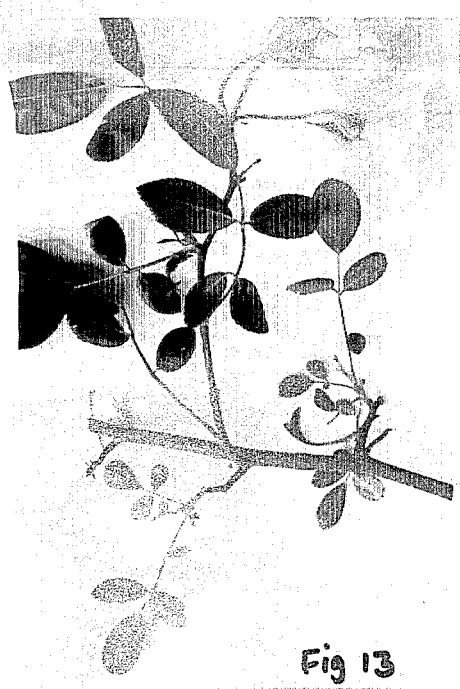
Fig 13
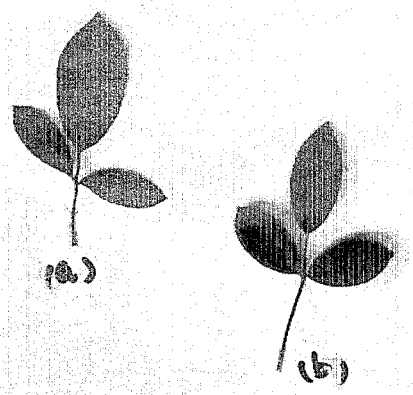
Fig. 14
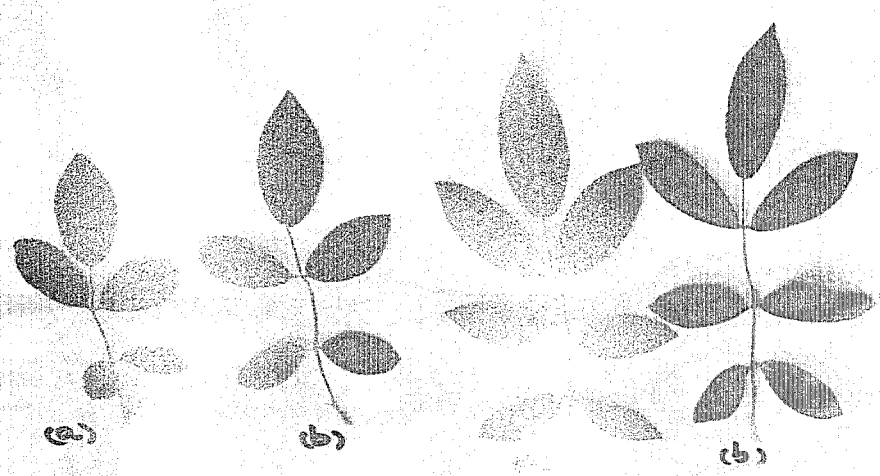
Fig. 15
Fig. 16